(12) United States Patent
Mori

(10) Patent No.: US 11,076,912 B2
(45) Date of Patent: Aug. 3, 2021

(54) BALLOON-TYPE ABLATION CATHETER AND ABLATION CATHETER DEVICE

(71) Applicant: Japan Lifeline Co., Ltd., Tokyo (JP)

(72) Inventor: Kenji Mori, Tokyo (JP)

(73) Assignee: Japan Lifeline Co., Ltd., Tokyo (JP)

( * ) Notice: Subject to any disclaimer, the term of this patent is extended or adjusted under 35 U.S.C. 154(b) by 197 days.

(21) Appl. No.: 15/679,912

(22) Filed: Aug. 17, 2017

(65) Prior Publication Data

US 2017/0354463 A1 Dec. 14, 2017

Related U.S. Application Data

(63) Continuation of application No. PCT/JP2016/057570, filed on Mar. 10, 2016.

(30) Foreign Application Priority Data

Mar. 27, 2015 (JP) .............................. JP2015-067650

(51) Int. Cl.
*A61B 18/14* (2006.01)
*A61B 18/00* (2006.01)
*A61M 25/01* (2006.01)

(52) U.S. Cl.
CPC .. *A61B 18/1492* (2013.01); *A61B 2018/0022* (2013.01); *A61B 2018/00023* (2013.01);
(Continued)

(58) Field of Classification Search
CPC ...... A61B 18/1492; A61B 2018/00023; A61B 2018/0022; A61B 2018/00238;
(Continued)

(56) References Cited

U.S. PATENT DOCUMENTS

| 2003/0120270 A1 | 6/2003 | Acker |
| 2007/0032787 A1 | 2/2007 | Hassett et al. |

(Continued)

FOREIGN PATENT DOCUMENTS

| JP | 2004-130096 | 4/2004 |
| JP | 2010-268847 | 12/2010 |
| JP | 2010-268933 | 12/2010 |

*Primary Examiner* — Eun Hwa Kim
*Assistant Examiner* — Adam Z Minchella
(74) *Attorney, Agent, or Firm* — Muramatsu & Associates

(57) ABSTRACT

It is an object of the present invention to provide a balloon-type ablation catheter that can measure the electric potential around the entire circumference of the pulmonary vein at a position near the left atrium with electrodes attached to a catheter distal end part of an electrode catheter inserted in a shaft in a state where a balloon is pressed against the area around the ostium of the pulmonary vein. The balloon-type ablation catheter of the present invention includes a catheter shaft (10) having a multi-lumen structure in which a plurality of lumens (11 to 17) are formed that include a liquid feeding lumen (13), (16) and an electrode catheter insertion lumen (12), a distal end tip (30) attached to the distal end of the catheter shaft (10), a balloon (50) attached to the distal end part of the catheter shaft (10), and a high-frequency current application electrode (70) provided in the balloon (50). A side hole (32) that communicates with the electrode catheter insertion lumen (12) and that opens on the side peripheral surface of the distal end tip (30) is formed in the distal end tip (30).

5 Claims, 16 Drawing Sheets

(52) U.S. Cl.
CPC ............... *A61B 2018/00083* (2013.01); *A61B 2018/00267* (2013.01); *A61B 2018/00375* (2013.01); *A61B 2018/00577* (2013.01); *A61B 2018/00642* (2013.01); *A61B 2018/00738* (2013.01); *A61B 2018/00839* (2013.01); *A61M 25/0147* (2013.01)

(58) Field of Classification Search
CPC .. A61B 2018/1475; A61B 2018/00267; A61B 2018/00375; A61B 2018/005776; A61B 2018/00642; A61B 2018/00738; A61B 2018/00839; A61M 25/0147
See application file for complete search history.

(56) References Cited

U.S. PATENT DOCUMENTS

| | | | |
|---|---|---|---|
| 2007/0083194 A1 | 4/2007 | Kunis et al. | |
| 2009/0018534 A1* | 1/2009 | Taimisto | A61B 18/1492 606/33 |
| 2010/0168737 A1 | 7/2010 | Grunewald | |
| 2012/0143177 A1 | 6/2012 | Avitall | |
| 2013/0066312 A1* | 3/2013 | Subramaniam | A61B 18/1492 606/33 |
| 2015/0157382 A1* | 6/2015 | Avitall | A61B 18/02 606/21 |
| 2015/0342675 A1* | 12/2015 | Highsmith | A61B 18/1492 606/41 |
| 2016/0175041 A1* | 6/2016 | Govari | A61B 18/1492 606/41 |

\* cited by examiner

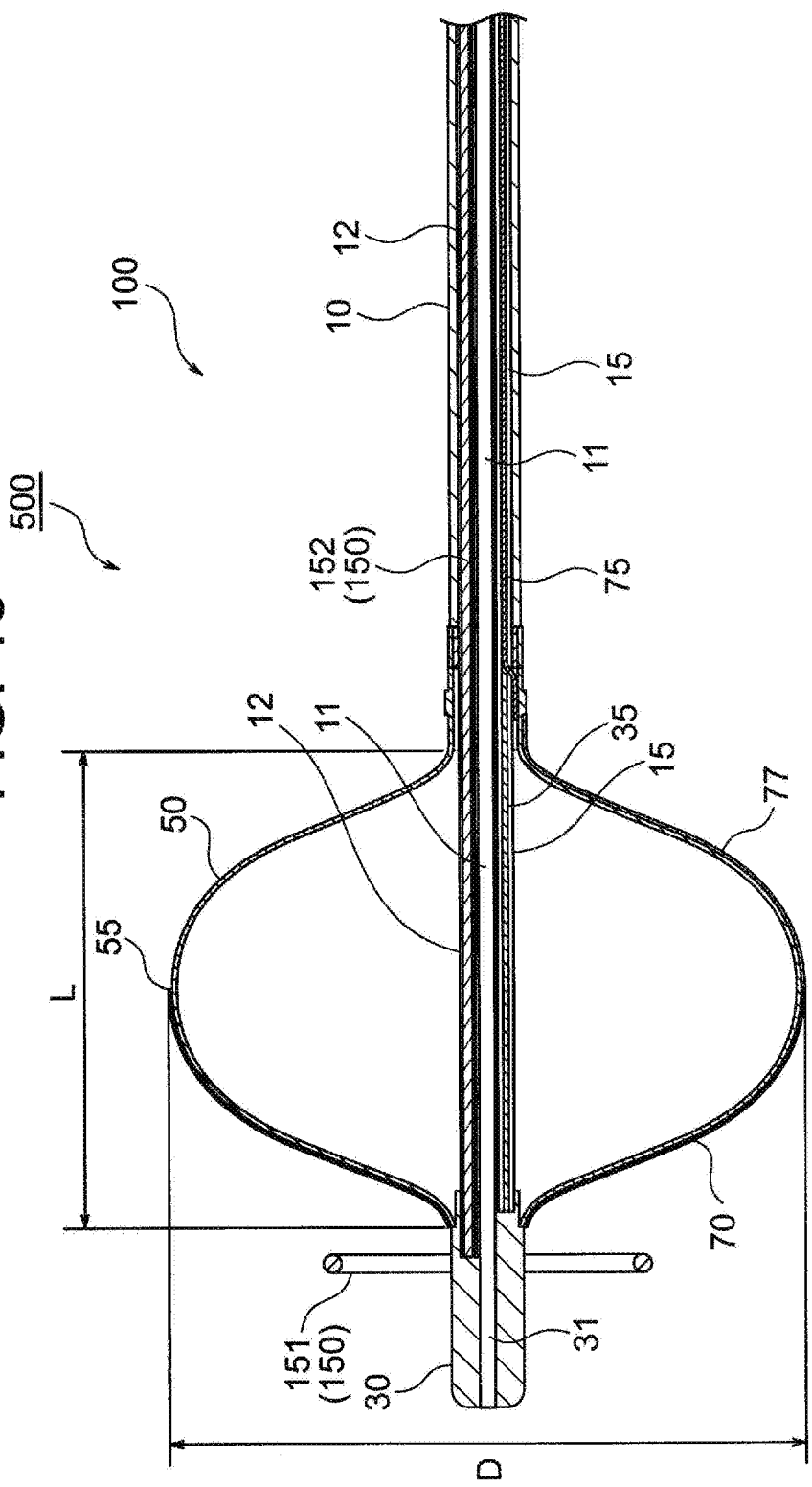

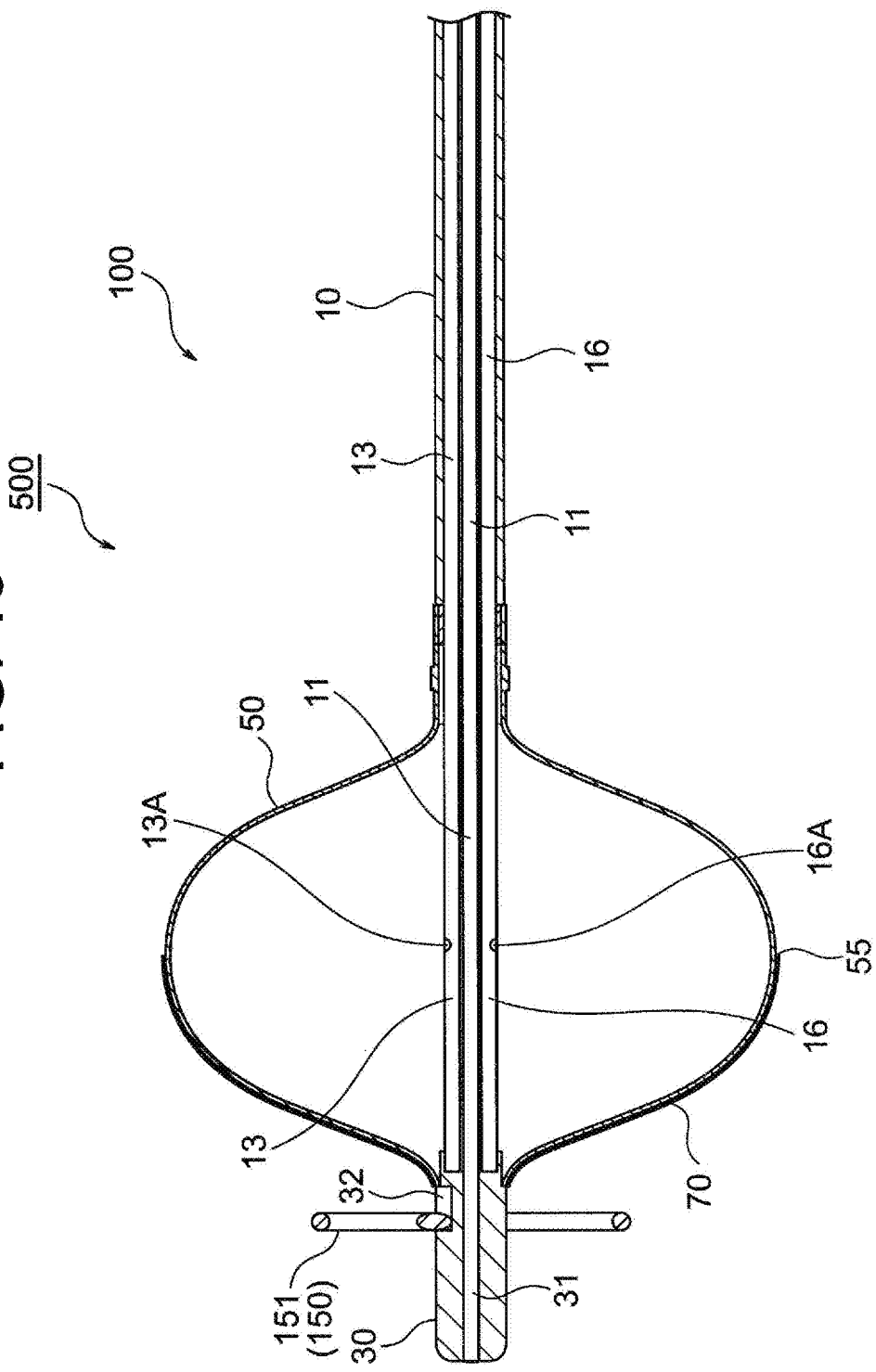

BALLOON-TYPE ABLATION CATHETER AND ABLATION CATHETER DEVICE

This is a continuation of International Application No. PCT/JP2016/057570 filed Match 10, 2010 which claims the foregin filing benefit based on Japanese Patent Application No. 2015-067650 filed Mar. 27, 2015, the entire contents of which are incorporated herein by reference.

TECHNICAL FIELD

The present invention relates to a balloon-type ablation catheter and an ablation catheter device, and more specifically, it relates to a balloon-type ablation catheter that electrically isolates the pulmonary vein, and an ablation catheter device including a balloon-type ablation catheter and an electrode catheter for measuring the electric potential around the entire circumference of the pulmonary vein.

BACKGROUND ART

Recently, as an ablation catheter for electrically isolating the pulmonary vein where the arrhythmia arises from the left atrium, there has been proposed a balloon-type ablation catheter including a catheter shaft, a balloon attached to the distal end side of the catheter shaft, and an in-balloon electrode and an in-balloon temperature sensor disposed inside the balloon (see, for example, Patent Literature 1).

According to such a balloon-type ablation catheter, the balloon attached to the distal end side of the catheter shaft is expanded by supplying liquid to the inside thereof, the expanded balloon is pressed against so as to cover the ostium of the pulmonary vein, high-frequency current is applied between the in-balloon electrode and a counter electrode plate, the liquid supplied to the inside of the balloon is heated (for example, to 60° C. or higher), the surface of the balloon is heated, and myocardial tissue around the ostium of the pulmonary vein in contact with the surface of the balloon (the joint between the pulmonary vein and the left atrium wall and the left atrium wall around the pulmonary vein) can thereby be ablated in an annular shape (planar shape).

Therefore, it is not necessary to repeat point-like ablation some dozen times in order to form an ablation line that isolates the pulmonary vein, one pulmonary vein can be isolated by a single ablation, and procedure time can be reduced and the burden on the patient can be reduced.

Now, when ablating the area around the ostium of the pulmonary vein with an ablation catheter, before and after the ablation (current application), the electric potential around the entire circumference of the pulmonary vein is measured with an electrode catheter having a ring-like catheter distal end part having a plurality of electrodes, and it is determined whether or not the pulmonary vein is successfully electrically isolated.

Hitherto, there has been proposed an ablation catheter device constituted by combining a balloon-type ablation catheter and an electrode catheter for measuring the electric potential around the entire circumference of the pulmonary vein having a ring-like catheter distal end part (see Patent Literature 2).

The ablation catheter device described in Patent Literature 2 includes a catheter shaft composed of a multi-lumen tube, an ablation assembly having a balloon attached to the distal end part of the catheter shaft, and a stabilization assembly (a catheter distal end part of an electrode catheter for measuring the electric potential around the entire circumference of the pulmonary vein) attached to a catheter on the distal end side of the ablation assembly.

In the ablation catheter device described in Patent Literature 2, the electrode catheter for measuring the electric potential around the entire circumference of the pulmonary vein is inserted into the catheter shaft of a balloon-type ablation catheter, and the catheter distal end part of the electrode catheter (stabilization assembly) extends from the distal end opening of a catheter extending from the distal end of the balloon.

CITATION LIST

Patent Literature

PTL 1: Japanese Unexamined Patent Application Publication No. 2010-268933
PTL 2: Japanese Unexamined Patent Application Publication No. 2004-130096

SUMMARY OF INVENTION

Technical Problem

The nearer to the ablation lesion formed around the ostium of the pulmonary vein, the more noticeable the change in the electric potential around the entire circumference of the pulmonary vein (disappearance of electric potential) caused by ablation treatment. Therefore, the measurement of the electric potential around the entire circumference of the pulmonary vein with the electrode catheter for measuring the electric potential around the entire circumference of the pulmonary vein is preferably performed on the left atrium side (at a position close to the ablation site) wherever possible.

However, in the ablation catheter described in Patent Literature 2, the separation distance between the ablation assembly for performing ablation and the stabilization assembly for measuring the electric potential around the entire circumference of the pulmonary vein (the catheter distal end part of the electrode catheter) is very long, and therefore, when the balloon that makes up the ablation assembly is pressed against the area around the ostium of the pulmonary vein (the joint between the pulmonary vein and the left atrium wall and the left atrium wall around the pulmonary vein) so as to cover the ostium of the pulmonary vein, the stabilization assembly is inserted significantly deeply into the pulmonary vein.

In such a case, even if appropriate ablation is performed with the ablation assembly, appropriate atrial electric potential cannot be measured with the stabilization assembly, and the effect of ablation treatment cannot be ascertained.

When ablation treatment is performed with an ablation catheter device such as that described in Patent Literature 2, it is possible, after the ablation (current application) for a given length of time, to retract the ablation catheter device and to locate the stabilization assembly in the vicinity of the ostium of the pulmonary vein.

However, such an operation is cumbersome, and it is desired to provide an ablation catheter that can immediately measure the electric potential around the entire circumference of the pulmonary vein with a stabilization assembly (catheter distal end part that makes up a ring-like multiple electrode catheter) without having to retract after ablation.

The present invention has been made based on the above circumstances.

It is an object of the present invention to provide a balloon-type ablation catheter into which an electrode catheter for measuring the electric potential around the entire circumference of the pulmonary vein having a ring-like catheter distal end part having a plurality of electrodes can be inserted, and that can measure the electric potential around the entire circumference of the pulmonary vein at a position near the left atrium (a position near the site ablated by the balloon) with a plurality of electrodes attached to the catheter distal end part of the electrode catheter inserted therein in a state where the expanded balloon is pressed against the area around the ostium of the pulmonary vein so as to cover the ostium of the pulmonary vein.

It is another object of the present invention to provide an ablation catheter device that includes a balloon-type ablation catheter, and an electrode catheter for measuring the electric potential around the entire circumference of the pulmonary vein inserted therein, and that can measure the electric potential around the entire circumference of the pulmonary vein at a position near the left atrium (a position near the site ablated by the balloon) with a plurality of electrodes attached to the catheter distal end part of the electrode catheter in a state where the expanded balloon of the balloon-type ablation catheter is pressed against the area around the ostium of the pulmonary vein so as to cover the ostium of the pulmonary vein.

Solution to Problem (1) The balloon-type ablation catheter of the present invention is an ablation catheter for electrically isolating the pulmonary vein, and includes a catheter shaft in which a plurality of lumens are formed that include a liquid feeding lumen for flowing liquid and an electrode catheter insertion lumen for inserting an electrode catheter for measuring electric potential, a distal end tip attached to the distal end of the catheter shaft, a balloon that is attached to the catheter shaft so as to contain the distal end part of the catheter shaft and that is expanded by supplying the inside thereof with liquid flowing through the liquid feeding lumen, and a high-frequency current application electrode that is provided inside the balloon, on the outer surface of the balloon, or in the wall of the balloon, and between which and a counter electrode plate attached to the body surface of a patient, high-frequency current is applied.

A side hole that communicates with the electrode catheter insertion lumen and that opens on the side peripheral surface of the distal end tip is formed in the distal end tip.

(2) In the balloon-type ablation catheter of the present invention, it is preferable that the distance (d) from the distal end of the balloon to the opening of the side hole be 4 mm or less.

(3) In the balloon-type ablation catheter of the present invention, it is preferable that the high-frequency current application electrode be composed of a metal thin film formed on at least part of the outer surface of the balloon, and that many irrigation through-holes leading from the inner surface of the balloon to the surface of the high-frequency current application electrode be formed in at least part of the formation region of the high-frequency current application electrode in order to irrigate the high-frequency current application electrode with liquid for expanding the balloon.

(4) In the balloon-type ablation catheter of the present invention, it is preferable that the distal end tip be an electrode.

(5) It is preferable that the balloon-type ablation catheter of the present invention be used for electrically isolating the pulmonary vein.

(6) The ablation catheter device of the present invention includes the balloon-type ablation catheter of the present invention, and an electrode catheter for measuring the electric potential around the entire circumference of the pulmonary vein inserted into the electrode catheter insertion lumen of the catheter shaft that makes up the balloon-type ablation catheter.

The electrode catheter includes a catheter main body, and a ring-like catheter distal end part connected to the distal end side of the catheter main body and having a plurality of electrodes.

The catheter distal end part of the electrode catheter is inserted into the side hole formed in the distal end tip of the balloon-type ablation catheter, and can be caused to extend from the opening of the side hole and can be retracted.

ADVANTAGEOUS EFFECTS OF INVENTION

According to the balloon-type ablation catheter of the present invention, the electric potential around the entire circumference of the pulmonary vein at a position near the left atrium (a position near the site ablated by the balloon) can be measured with the plurality of electrodes attached to the catheter distal end part of the electrode catheter inserted into the electrode catheter insertion lumen in a state where the expanded balloon is pressed against the area around the ostium of the pulmonary vein so as to cover the ostium of the pulmonary vein, and the effect of ablation treatment can be reliably ascertained from the change in the electric potential around the entire circumference of the pulmonary vein before and after ablation (current application).

According to the ablation catheter device of the present invention, the electric potential around the entire circumference of the pulmonary vein at a position near the left atrium (a position near the site ablated by the balloon) can be measured with the plurality of electrodes attached to the catheter distal end part of the electrode catheter in a state where the expanded balloon in the ablation catheter is pressed against the area around the ostium of the pulmonary vein so as to cover the ostium of the pulmonary vein, and the effect of ablation treatment can be reliably ascertained from the change in the electric potential around the entire circumference of the pulmonary vein before and after ablation (current application).

BRIEF DESCRIPTION OF DRAWINGS

FIG. 15 is a longitudinal sectional view of the distal end part of the ablation catheter device shown in FIG. 10 (a sectional view taken along line XV-XV of FIG. 14).

FIG. 16 is a longitudinal sectional view of the distal end part of the ablation catheter device shown in FIG. 10 (a sectional view taken along line XVI-XVI of FIG. 14).

DESCRIPTION OF EMBODIMENTS

<Balloon-Type Ablation Catheter>

Figure 1:
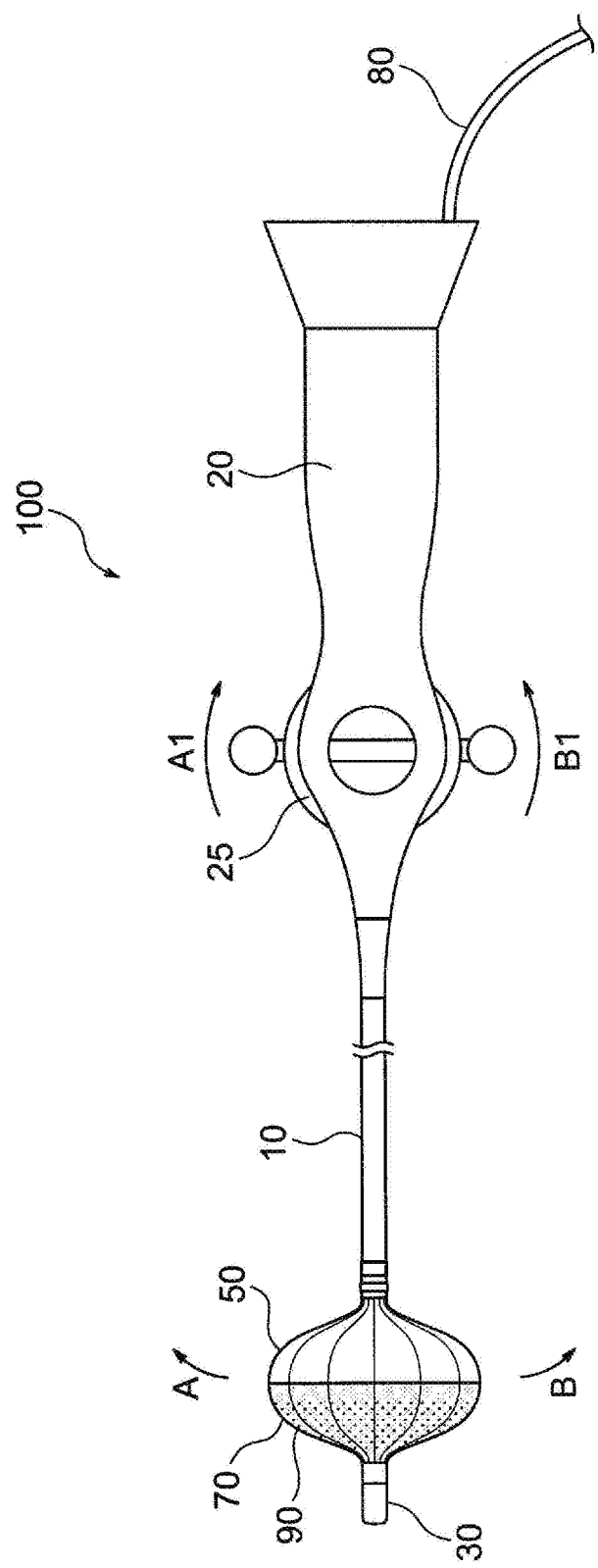
FIG. 1 is a schematic front view showing an embodiment of an ablation catheter of the present invention.
Figure 2:
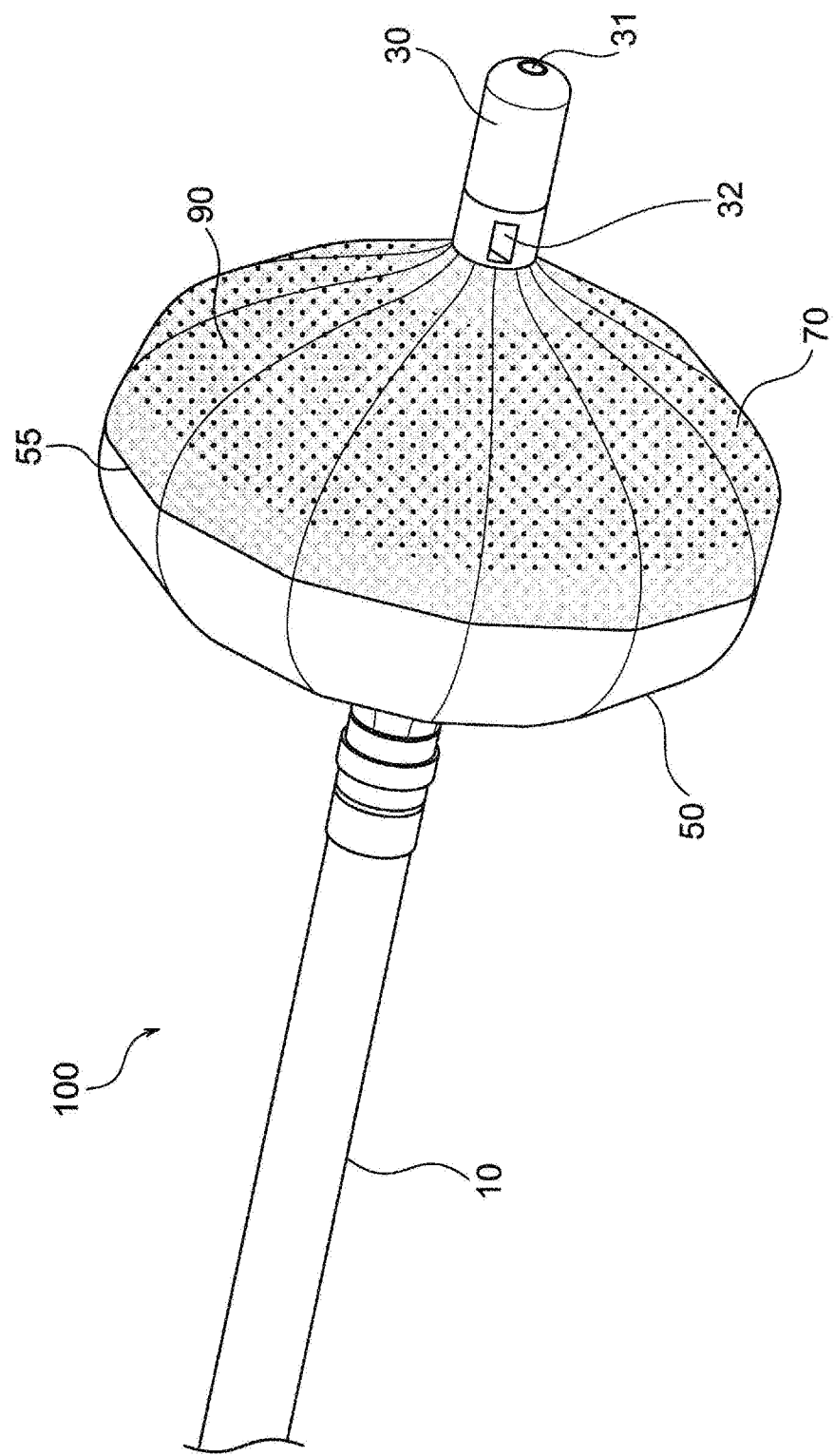
FIG. 2 is a perspective view showing the distal end part of the ablation catheter shown in FIG. 1.
Figure 3:
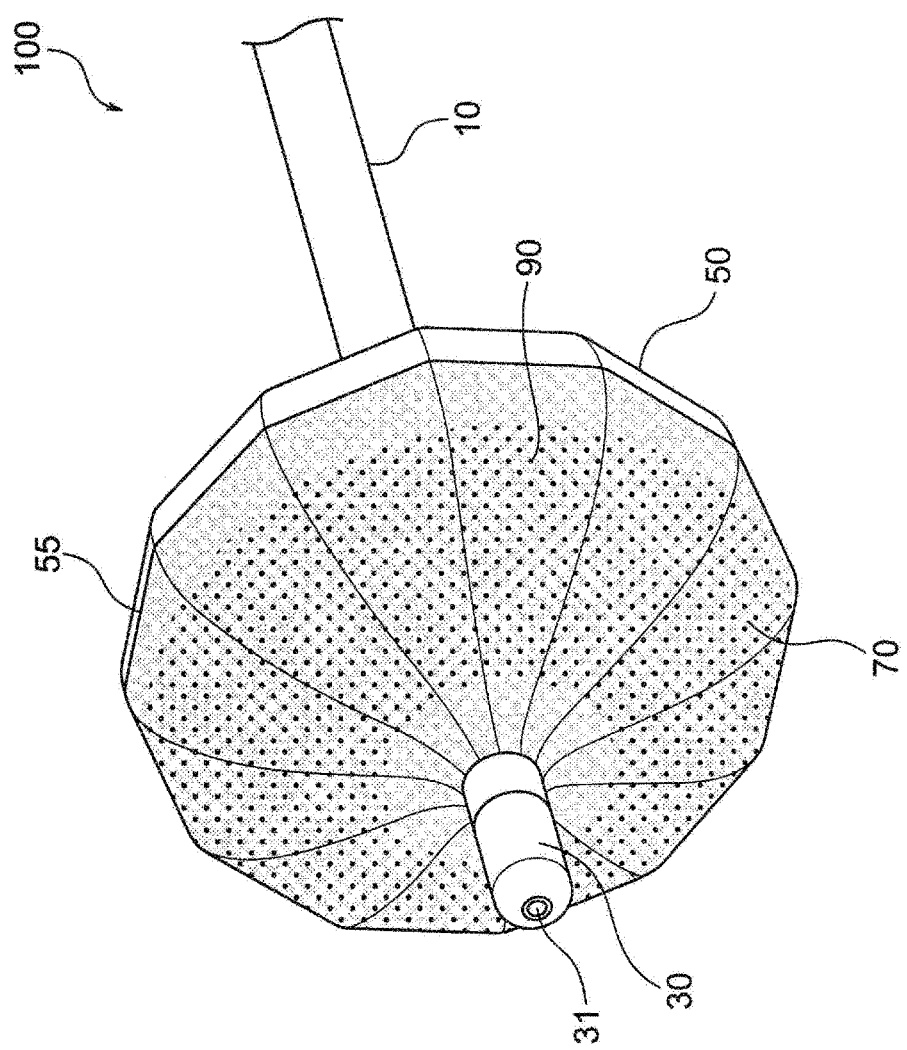
FIG. 3 is a perspective view showing the distal end part of the ablation catheter shown in FIG. 1.

A balloon-type ablation catheter 100 of this embodiment shown in FIGS. 1 to 8 is an ablation catheter for electrically isolating the pulmonary vein, and includes a catheter shaft 10 composed of a resin multi-lumen tube in which seven lumens 11 to 17 are formed that include liquid feeding lumens (third lumen 13 and sixth lumen 16) for flowing saline, and an electrode catheter insertion lumen (second lumen 12) for inserting an electrode catheter for measuring the electric potential, a control handle 20 connected to the proximal end of the catheter shaft 10, a distal end tip 30 attached to the distal end of the catheter shaft 10, a conductor (a lead wire) 35 that is electrically connected to the distal end tip 30 and that is inserted into a fifth lumen 15 of the catheter shaft 10, a first operation wire 41 that is inserted into a fourth lumen 14 of the catheter shaft 10 and the proximal end of which can be operationally pulled, a second operation wire 42 that is inserted into a seventh lumen 17 of the catheter shaft 10 and the proximal end of which can be pulled, a balloon 50 that is attached to the catheter shaft 10 so as to contain the distal end part of the catheter shaft 10 and that is expanded by supplying the inside thereof with saline flowing through the third lumen 13 and/or the sixth lumen 16 that are the liquid feeding lumens of the catheter shaft 10, a high-frequency current application electrode 70 (balloon surface electrode) that is composed of a thin film of gold formed on at least part of the outer surface of the balloon 50 (the outer surface on the distal end side of a maximum diameter part 55), and between which and a counter electrode plate attached to the body surface of a patient, high-frequency current is applied, a conductor (a lead wire) 75 that is electrically connected to the high-frequency current application electrode 70 and that is inserted into the fifth lumen 15 of the catheter shaft 10, and an injection tube 80 for supplying saline to the liquid feeding lumens (third lumen 13 and sixth lumen 16) of the catheter shaft 10. Many irrigation through-holes 90 leading from the inner surface of the balloon 50 to the surface of the high-frequency current application electrode 70 (through the wall of the balloon 50 and the thin film that makes up the high-frequency current application electrode 70) are formed in at least part of the formation region of the high-frequency current application electrode 70 in order to irrigate the high-frequency current application electrode 70 with saline for expanding the balloon 50. A side hole 32 that communicates with the electrode catheter insertion lumen (second lumen 12) of the catheter shaft 10 and that opens on the side peripheral surface of the distal end tip 30 is formed in the distal end tip 30.

As shown in FIGS. 5 to 8, seven lumens are formed in the catheter shaft 10 that makes up the ablation catheter 100.

A first lumen 11 of the catheter shaft 10 is a guide wire lumen, and a guide wire is inserted into the first lumen 11 (as described later, a guide wire may be used so that the ablation catheter 100 can be easily brought to the left atrium (LA)).

Figure 5:
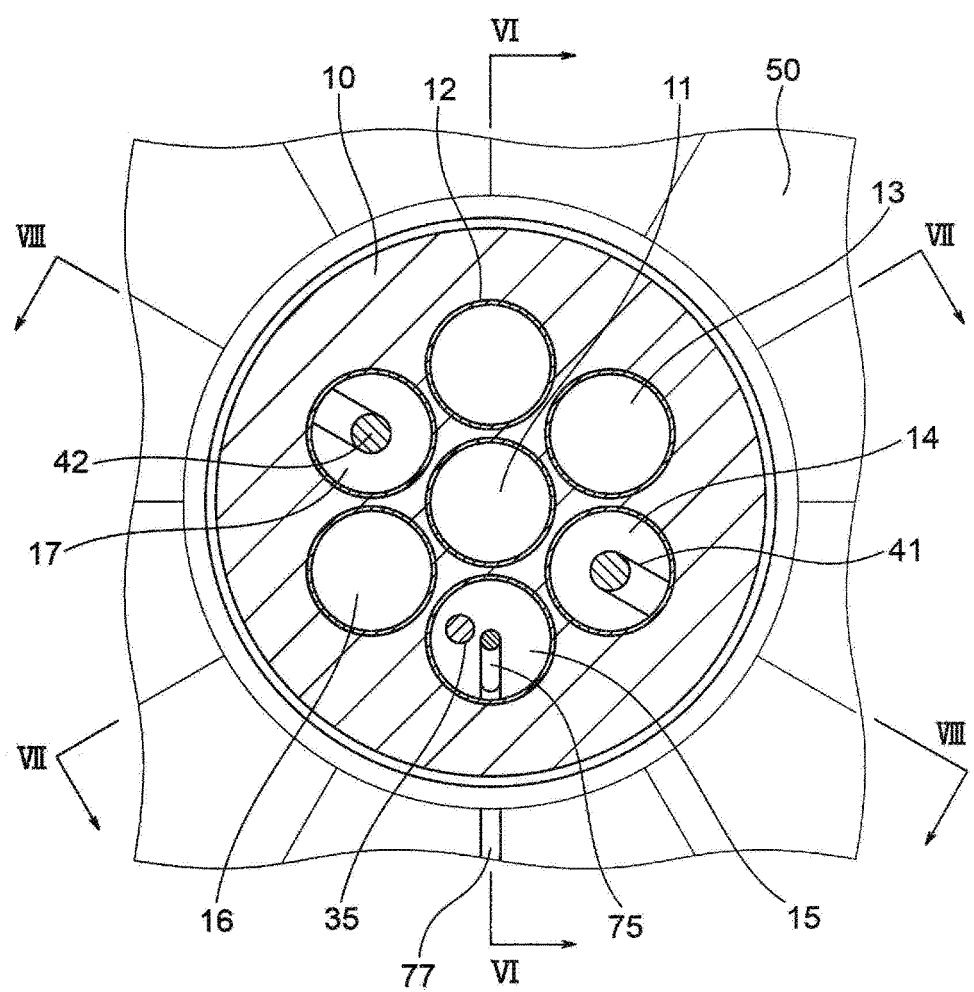
FIG. 5 is a cross-sectional view of the distal end part of the ablation catheter shown in FIG. 1.
Figure 6:
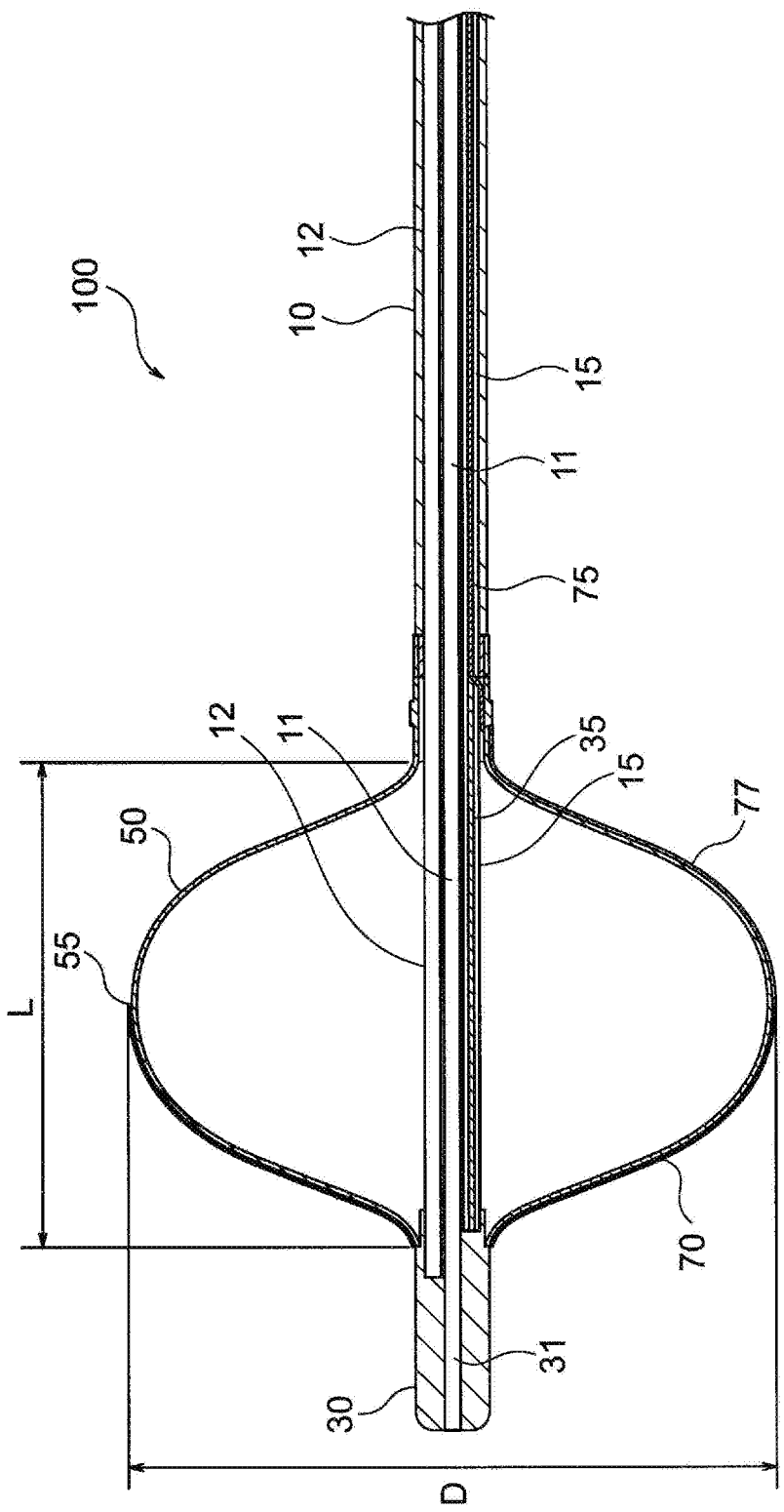
FIG. 6 is a longitudinal sectional view of the distal end part of the ablation catheter shown in FIG. 1 (a sectional view taken along line VI-VI of FIG. 5).

The second lumen 12 shown in FIGS. 5 and 6 is an electrode catheter insertion lumen, and an electrode catheter for measuring the electric potential around the entire circumference of the pulmonary vein (the electric potential throughout the inner peripheral part of the pulmonary vein) is inserted into the second lumen.

Figure 7:
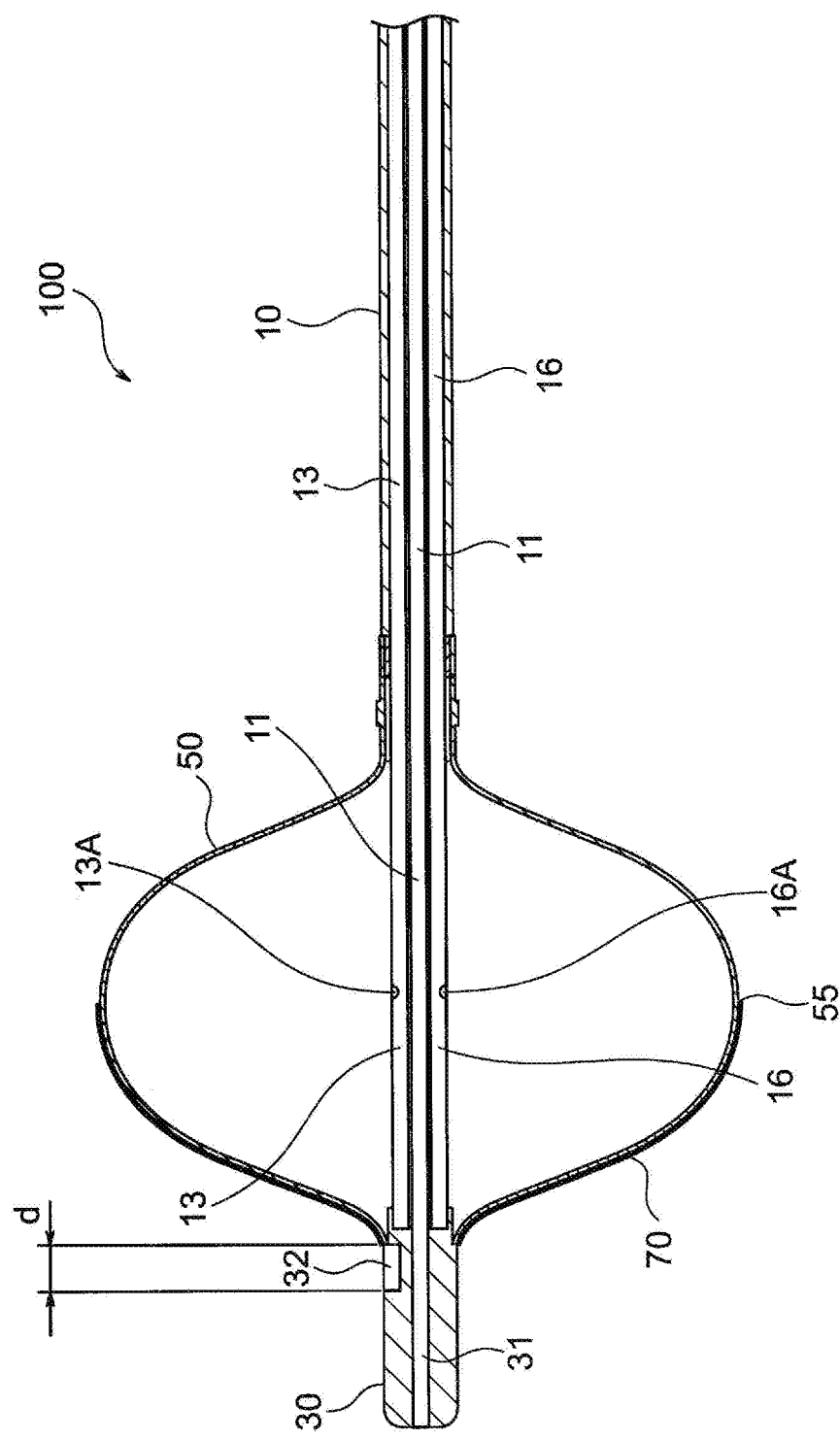
FIG. 7 is a longitudinal sectional view of the distal end part of the ablation catheter shown in FIG. 1 (a sectional view taken along line VII-VII of FIG. 5).

The third lumen 13 and the sixth lumen 16 shown in FIGS. 5 and 7 are liquid feeding lumens, and saline for expanding the balloon 50 is flown through at least one of the third lumen 13 and the sixth lumen 16.

By discharging saline flowing through the third lumen 13, from an opening 13A formed in the outer peripheral surface of the distal end part of the catheter shaft 10, or by discharging saline flowing through the sixth lumen 16, from an opening 16A formed in the outer peripheral surface of the distal end part of the catheter shaft 10, saline is supplied to the inside of the balloon 50 containing the distal end part of the catheter shaft 10, and the balloon 50 can thereby be expanded.

Saline may be discharged from one of the opening 13A and the opening 16A into the balloon 50, and saline in the balloon 50 may be returned to the lumen through the other of the opening 13A and the opening 16A.

Figure 8:
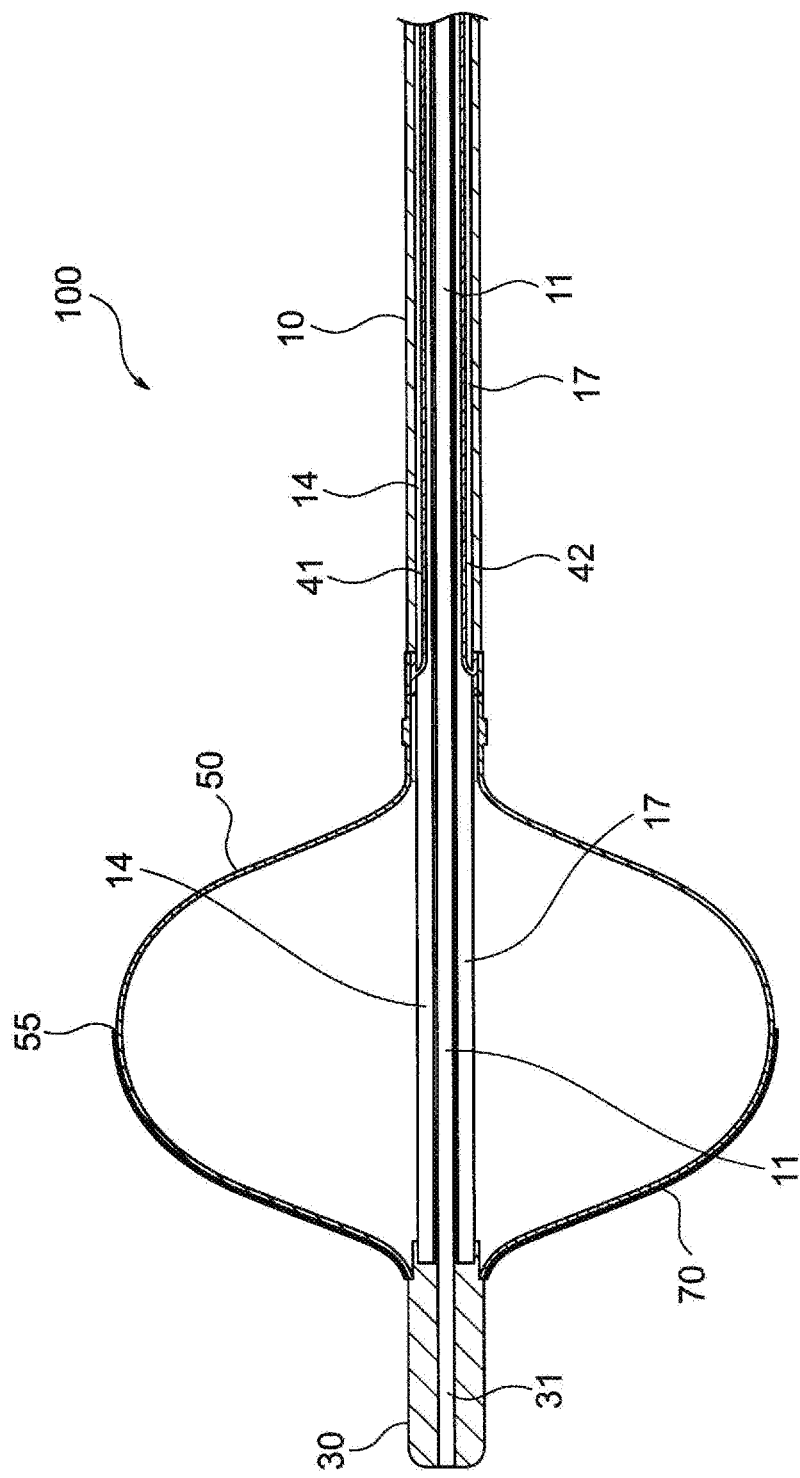
FIG. 8 is a longitudinal sectional view of the distal end part of the ablation catheter shown in FIG. 1 (a sectional view taken along line VIII-VIII of FIG. 5).

The fourth lumen 14 and the seventh lumen 17 shown in FIGS. 5 and 8 are operation wire insertion lumens, the first operation wire 41 is inserted into the fourth lumen 14, and the second operation wire 42 is inserted into the seventh lumen 17.

The fifth lumen 15 shown in FIGS. 5 and 6 is a lumen for inserting a conductor, and the conductor 75 of the high-frequency current application electrode 70 and the conductor 35 of the distal end tip 30 are inserted into the fifth lumen 15.

The outside diameter of the catheter shaft 10 is usually 2.0 to 5.0 mm.

The length of the catheter shaft 10 is usually 600 to 1500 mm. Constituent materials of the catheter shaft 10 include thermoplastic resins such as polyamide, polyether polyamide, polyurethane, polyether block amide (PEBAX) (registered trademark), and nylon. Among these, PEBAX is preferable.

The control handle 20 is connected to the proximal end of the catheter shaft 10.

A connector (not shown) having a plurality of terminals is provided inside the control handle 20 that makes up the ablation catheter 100, and the proximal end of the conductor 75 of the high-frequency current application electrode 70 and the proximal end of the conductor 35 of the distal end tip 30 are connected to the terminals of the connector.

A knob 25 for performing the operation of bending the distal end part of the catheter shaft 10 is attached to the control handle 20.

As shown in FIG. 8, the distal end of each of the first operation wire 41 and the second operation wire 42 is fixed to the distal end part of the catheter shaft 10 (slightly on the proximal end side of the proximal end position of the balloon 50).

On the other hand, the proximal end of each of the first operation wire 41 and the second operation wire 42 is connected to the knob 25 of the control handle 20.

Therefore, by rotating the knob 25 of the control handle 20 in the direction shown by arrow A1 in FIG. 1 to operationally pull the first operation wire 41, the distal end part of the catheter shaft 10 can be bent in a first direction (the direction shown by arrow A in the figure).

By rotating the knob 25 of the control handle 20 in the direction shown by arrow B1 in FIG. 1 to operationally pull the second operation wire 42, the distal end part of the catheter shaft 10 can be bent in a second direction (the direction shown by arrow B in the figure).

The balloon 50 that makes up the ablation catheter 100 is attached to the catheter shaft 10 so as to contain the distal end part (a part in the lengthwise direction of the distal end part) of the catheter shaft 10.

The balloon 50 is expanded by supplying the inside thereof with saline flowing through the liquid feeding lumens (the third lumen 13 and/or the sixth lumen 16) of the catheter shaft 10, and the expanded balloon 50 is pressed against the area around the ostium of the pulmonary vein (the joint between the pulmonary vein and the left atrium wall and the left atrium wall around the pulmonary vein) so as to cover the ostium of the pulmonary vein.

The same constituent materials as those of a balloon that makes up a conventionally known balloon catheter can be used as constituent materials of the balloon 50, and polyurethane polymer materials are more preferable.

Polyurethane polymer materials include, for example, thermoplastic polyether urethane, polyether polyurethane urea, fluorine polyether urethane urea, polyether polyurethane urea resin, and polyether polyurethane urea amide.

The shape of the balloon 50 is not particularly limited as long as it can fit the area around the ostium of the pulmonary vein, and is preferably a substantially spheroidal shape, and more specifically, the shape of a spheroid obtained by rotating an ellipse about its minor axis (oblate spheroid).

In the balloon 50 having a substantially spheroidal (oblate spheroidal) shape, the diameter at the time of expansion (the balloon diameter D shown in FIG. 6) is preferably 5 to 50 mm, and more preferably 10 to 35 mm.

The length of the balloon 50 at the time of expansion (the balloon length L shown in FIG. 6) is preferably 1 to 15 mm, and more preferably 5 to 10 mm.

The ratio of the balloon diameter (D) to the balloon length (L) (D/L) is preferably 1.1 to 5.0, and more preferably 1.5 to 3.0.

Since the value of the ratio (D/L) is 1.1 or more, the balloon easily fits the area around the ostium of the pulmonary vein (the joint between the pulmonary vein and the left atrium wall and the left atrium wall around the pulmonary vein), and the area around the ostium of the pulmonary vein can be ablated in an annular shape with the high-frequency current application electrode 70 described later.

In the case of a balloon whose value of the ratio (D/L) is less than 1.1, when pressing this against the area around the ostium of the pulmonary vein, it may be inserted deeply into the pulmonary vein, and ablation at that position may cause pulmonary venous stenosis.

On the other hand, when the value of the ratio (D/L) is greater than 5.0, the outside diameter (wrapping diameter) when such a balloon is folded and wrapped around the catheter shaft may be excessive.

The high-frequency current application electrode 70 that makes up the ablation catheter 100 is composed of a thin film of gold formed on the outer surface on the distal end side of the maximum diameter part 55 of the balloon 50.

The film thickness of the thin film that makes up the high-frequency current application electrode 70 is preferably 2.5 to 10.0 μm, and more preferably 3.0 to 5.0 μm.

When this film thickness is less than 2.5 μm, during the procedure (during high-frequency current application), the high-frequency current application electrode composed of a thin film may heat up due to Joule heat.

On the other hand, when the film thickness of the thin film is greater than 10.0 μm, it is hard for the thin film (high-frequency current application electrode) to follow the change of form of the balloon during expansion and contraction, and the expandability and contractility of the balloon may be impaired.

The method for forming the thin film of gold that makes up the high-frequency current application electrode 70 on the outer surface of the balloon 50 is not particularly limited, and a usual thin film formation method, such as vapor deposition, sputtering, or plating, can be used.

The high-frequency current application electrode 70 is formed on the outer surface on the distal end side of the maximum diameter part 55 of the balloon 50, and is not formed on the outer surface on the proximal end side of the maximum diameter part 55.

Therefore, the proximal end side surface of the balloon 50, which is virtually not used in ablation (need not be heated), does not become hot, and formation of a blood clot in the vicinity of the proximal end side surface of the balloon 50, and ablation of a healthy site in contact with the proximal end side surface of the balloon 50 can be avoided.

In addition, since the high-frequency current application electrode 70 is formed only on the distal end side outer surface of the balloon 50, the distal-proximal position of the balloon 50 can be easily grasped from a radiographic image (cardiac CINE image).

According to the ablation catheter 100 of this embodiment, by high-frequency current applied between the balloon surface electrode 70 and a counter electrode plate attached to the body surface of a patient, even the deep part of the myocardial tissue in contact with the balloon surface electrode 70 can be sufficiently heated (high-frequency heated), and therefore a lesion (ablation lesion) leading from the surface of the myocardial tissue to the deep part thereof can be reliably formed.

Furthermore, in the case of conventional balloon-type ablation, liquid in a balloon is heated to about 60° C., and the myocardium surface is ablated by that heat. Therefore, although the myocardium surface in contact with the balloon is ablated, that heat is less likely to be sufficiently transferred to the deep part. In contrast, in the case of high-frequency heating, the myocardial tissue is heated by high-frequency current between a counter electrode plate on the body surface (for example, one attached to the whole surface of the back of a patient) and a balloon surface electrode. Therefore, high-frequency current flows toward the deep part as seen from the myocardial tissue. Due to the difference in surface area between the counter electrode plate and the balloon surface electrode, when high-frequency current is applied, the current density near the myocardial tissue increases, and heating of the vicinity of the myocardial tissue (toward the deep part) is performed. Therefore, in the case of high-frequency heating, a lesion toward the deep part of the myocardium is reliably formed.

Figure 4:
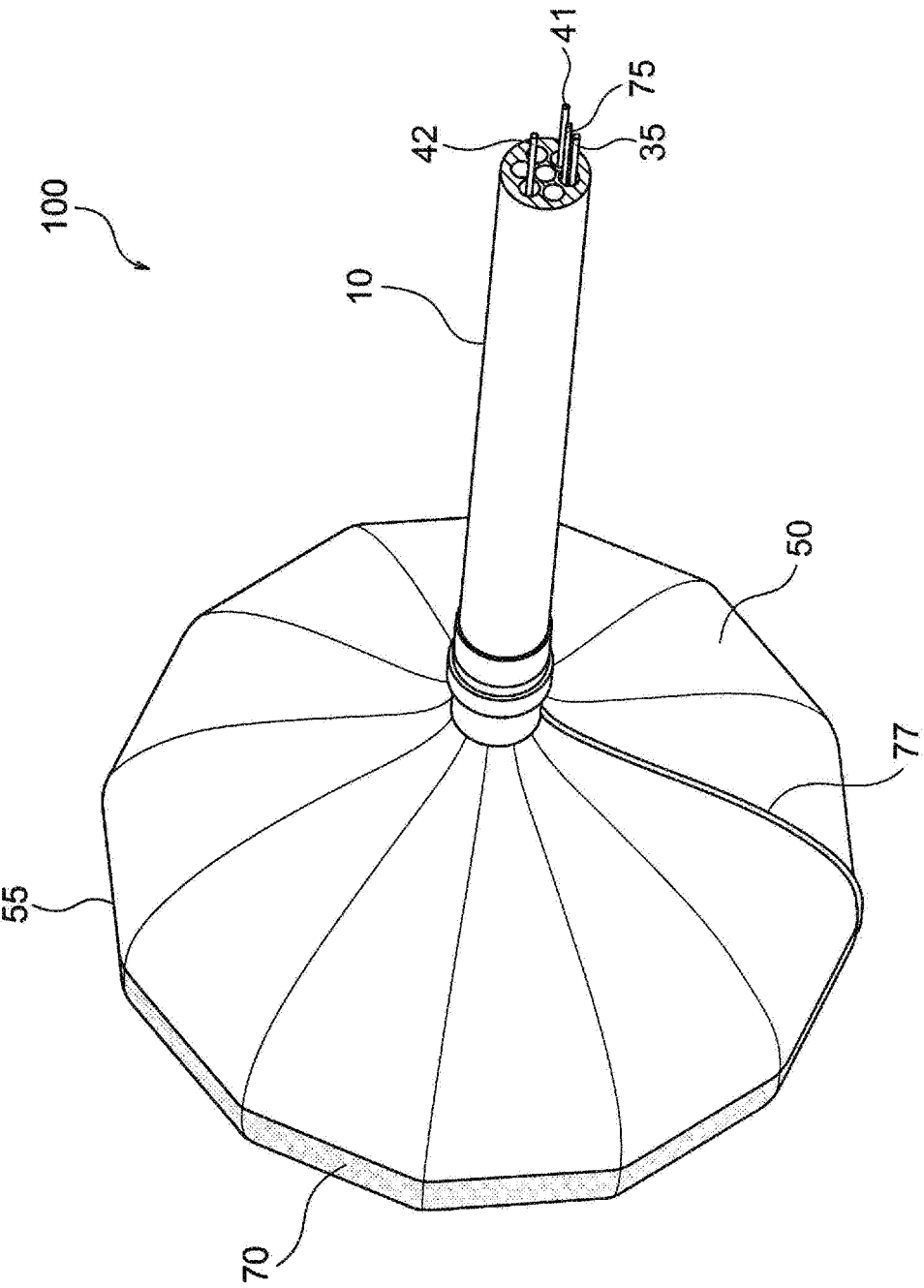
FIG. 4 is a perspective view showing the distal end part of the ablation catheter shown in FIG. 1.

The conductor 75 (the conductor of the high-frequency current application electrode 70) that makes up the ablation catheter 100 is inserted into the fifth lumen 15 of the catheter shaft 10, and its distal end is connected to the high-frequency current application electrode 70 through a lead 77 composed of a metal thin film shown in FIGS. 4 to 6.

On the other hand, the proximal end of the conductor 75 is connected to a connector disposed inside the control handle 20.

Constituent materials of the conductor 75 include, for example, copper, silver, gold, platinum, tungsten, and alloys of these metals, and, in terms of preventing short circuit, the conductor 75 is preferably coated with an electrical insulating protective coating of fluorine resin or the like.

The distal end tip 30 attached to the distal end of the catheter shaft 10 and making up the ablation catheter 100 is located on the distal end side of the distal end of the balloon 50 containing the distal end part of the catheter shaft 10.

High-frequency current can be applied between the distal end tip 30 and a counter electrode plate attached to the body surface of a patient, and, as with the conventionally known ablation catheter, point-like ablation (spot ablation) can be performed. Therefore, when the pulmonary vein cannot be completely isolated by ablation with the high-frequency current application electrode 70 (for example, when the high-frequency current application electrode 70 cannot sufficiently fit the area around the ostium of the pulmonary vein), touch-up can be performed by performing ablation with the distal end tip 30.

The outside diameter of the distal end tip 30 is usually 2.0 to 5.0 mm.

The length of the distal end tip 30 extending from the distal end of the balloon 50 is usually greater than 4 mm and less than or equal to 10.0 mm.

Constituent materials of the distal end tip 30 include, for example, gold, silver, platinum, copper, and alloys of these metals. The whole distal end tip 30 need not be made of metal, and the proximal end part of the distal end tip 30 may be made of resin. Resin constituent materials in this case include thermoplastic resins such as polyamide, polyether polyamide, polyurethane, polyether block amide (PEBAX) (registered trademark), and nylon, and thermosetting resins such as silicone.

As shown in FIGS. 2, 3, and 6 to 8, the distal end tip 30 has a guide wire lumen 31 (through-hole) formed on the central axis thereof and communicating with the guide wire lumen (first lumen 11) of the catheter shaft 10.

The distal end tip 30 has a side hole 32 formed therein that communicates with the electrode catheter insertion lumen (second lumen 12) of the catheter shaft 10 and opens on the side peripheral surface of the distal end tip 30.

Since the electrode catheter insertion lumen (second lumen 12) is formed in the catheter shaft 10 that makes up the ablation catheter 100, and the side hole 32 that communicates with this electrode catheter insertion lumen and opens on the side peripheral surface is formed in the distal end tip 30, an electrode catheter for measuring the electric potential around the entire circumference of the pulmonary vein can be inserted into the electrode catheter insertion lumen (second lumen 12) of the catheter shaft 10, and the catheter distal end part of this electrode catheter can be caused to extend from the opening of the side hole 32.

As described above, the length of the distal end tip 30 is usually greater than 4 mm.

Therefore, when the catheter distal end part of the electrode catheter is caused to extend from the distal end of the distal end tip 30 (for example, the opening of the guide wire lumen 31), the separation distance between the balloon 50 (high-frequency current application electrode 70) performing ablation and the electrode attached to the catheter distal end part (electrode for measuring the electric potential around the entire circumference of the pulmonary vein) is long, and therefore appropriate atrial electric potential cannot be measured.

In the ablation catheter 100 of this embodiment, since the distal end part of the electrode catheter can be caused to extend from the opening of the side hole 32 located in the vicinity of the distal end of the balloon 50, appropriate atrial electric potential can be measured with an electrode attached to the catheter distal end part extending from the opening of the side hole 32. The effect of ablation treatment can thereby be reliably ascertained.

In terms of ascertaining the effect of the ablation, the distance from the distal end of the balloon 50 to the opening (opening edge) of the side hole 32 (the distance d shown in FIG. 7) is preferably short. The distance d is preferably 4.0 mm or less, and more preferably 2.0 mm or less.

The conductor 35 (the conductor of the distal end tip 30) that makes up the ablation catheter 100 is inserted into the fifth lumen of the catheter shaft 10, extends from the fifth lumen, and is connected and fixed to the distal end tip 30.

On the other hand, the proximal end of the conductor 35 is connected to a connector disposed inside the control handle 20.

The same metals and alloys as for the conductor 75 can be used as constituent materials of the conductor 35, and the conductor 35 is preferably coated with an electrical insulating protective coating.

In the ablation catheter 100 of this embodiment, in the formation region of the high-frequency current application electrode 70 except for the vicinity of the distal end of the balloon 50 and the vicinity of the maximum diameter part 55, in order to irrigate the high-frequency current application electrode 70 with saline for expanding the balloon 50, many irrigation through-holes 90 are formed that lead from the inner surface of the balloon 50 to the surface of the high-frequency current application electrode 70 (through the wall of the balloon 50 and the thin film).

The hole diameter of the irrigation through-holes 90 is not particularly limited, and is, for example, 5 to 80 μm.

The formation density of the irrigation through-holes 90 is not particularly limited, either, and is, for example, 10 to 100 per cm$^2$.

Examples of the method for forming the irrigation through-holes 90 (hole making method) include laser processing and punching process.

The formation of the irrigation through-holes 90 is preferably performed on a sheet-like balloon formation material on the surface of which a thin film to become the high-frequency current application electrode 70 is formed.

Figure 9:
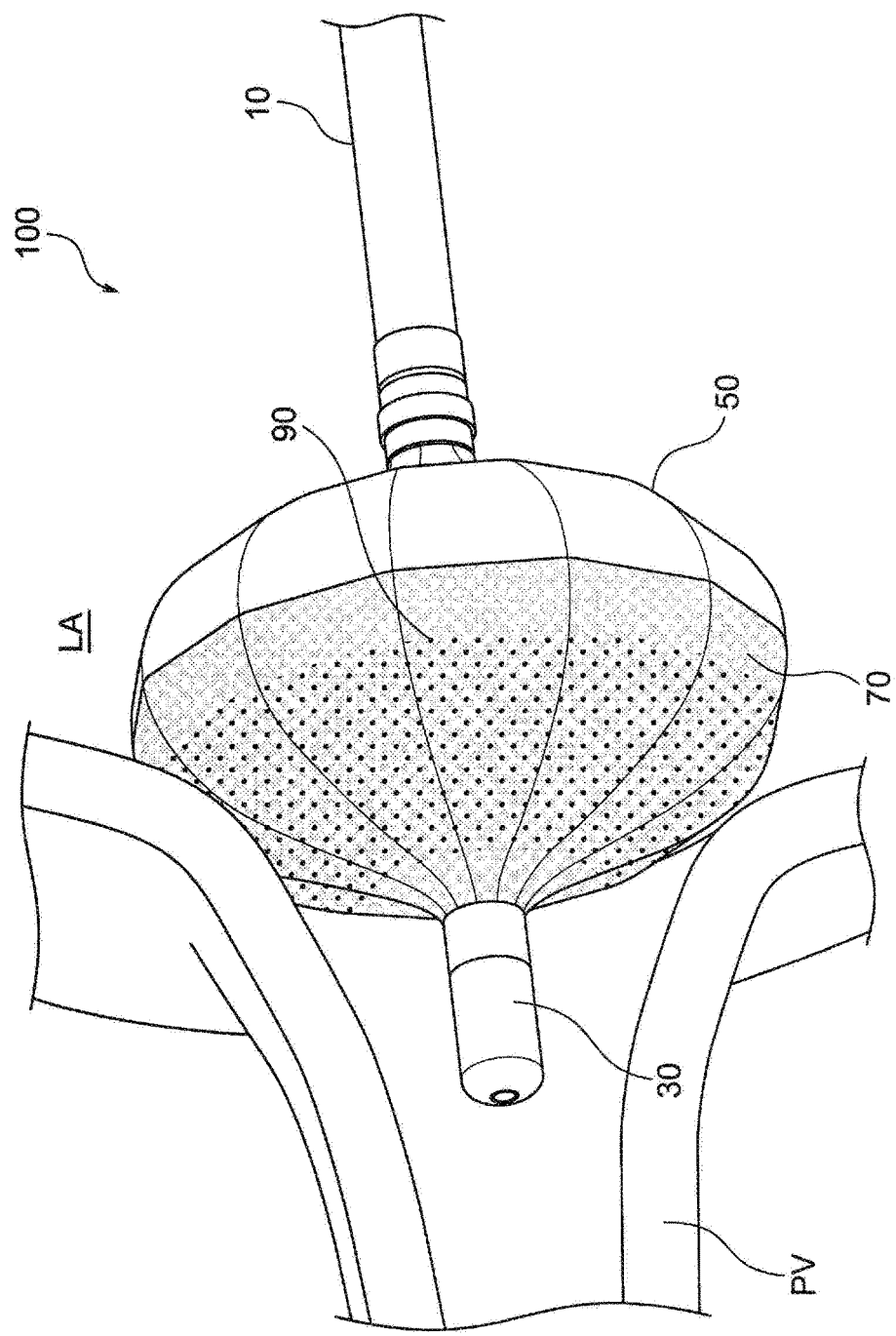
FIG. 9 is a perspective view showing the ablation catheter shown in FIG. 1 in use.

In the ablation treatment (procedure) performed using the ablation catheter 100 of this embodiment, the balloon 50 of the ablation catheter 100 is brought to the left atrium (LA) along a guide wire preliminarily inserted into the left atrium (LA), the high-frequency current application electrode 70 formed on the outer surface of the balloon 50 is pressed against the area around the ostium of the target pulmonary vein (the joint between the pulmonary vein (PV) and the left atrium wall and the left atrium wall around the pulmonary vein) as shown in FIG. 9, and high-frequency current is applied between this high-frequency current application electrode 70 and a counter electrode plate attached to the body surface of a patient. The current application time is usually about 10 to 120 seconds. The area around the ostium of the pulmonary vein is thereby ablated in an annular shape.

According to the ablation catheter 100 of this embodiment, since the catheter distal end part of the electrode catheter inserted into the electrode catheter insertion lumen (second lumen 12) can be caused to extend from the opening of the side hole 32 in a state where the expanded balloon 50 is pressed against the area around the ostium of the pulmonary vein so as to cover the ostium of the pulmonary vein, the electric potential around the entire circumference of the pulmonary vein at a position near the left atrium (a position near the ablation site) can be measured with the plurality of electrodes attached to the catheter distal end part, and the effect of ablation treatment can be reliably ascertained from the change in the electric potential around the entire circumference of the pulmonary vein before and after ablation (current application) (disappearance of abnormal electric potential after appropriate ablation).

<Ablation Catheter Device>

Next, an embodiment of an ablation catheter device of the present invention will be described.

An ablation catheter device 500 of this embodiment shown in FIGS. 10 to 16 includes the above-described ablation catheter 100 and an electrode catheter 150 for measuring the electric potential around the entire circumference of the pulmonary vein.

Figure 14:
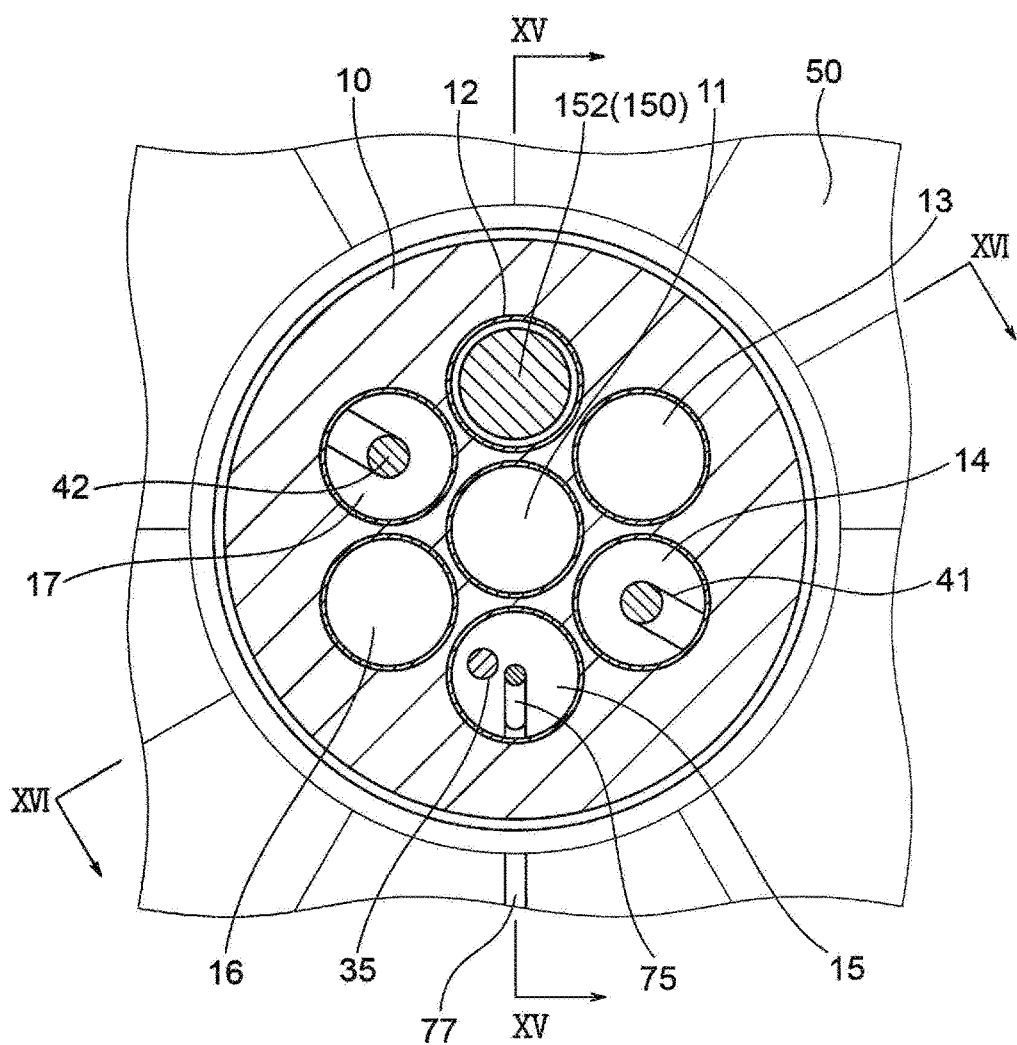
FIG. 14 is a cross-sectional view of the distal end part of the ablation catheter device shown in FIG. 10.

The electrode catheter 150 that makes up the ablation catheter device 500 includes a catheter main body 152, and a ring-like (circular loop-like) catheter distal end part 151 connected to the distal end side of the catheter main body 152, and is inserted into the electrode catheter insertion lumen (second lumen 12) formed in the catheter shaft 10 of the ablation catheter 100 as shown in FIGS. 14 and 15.

Figure 10:
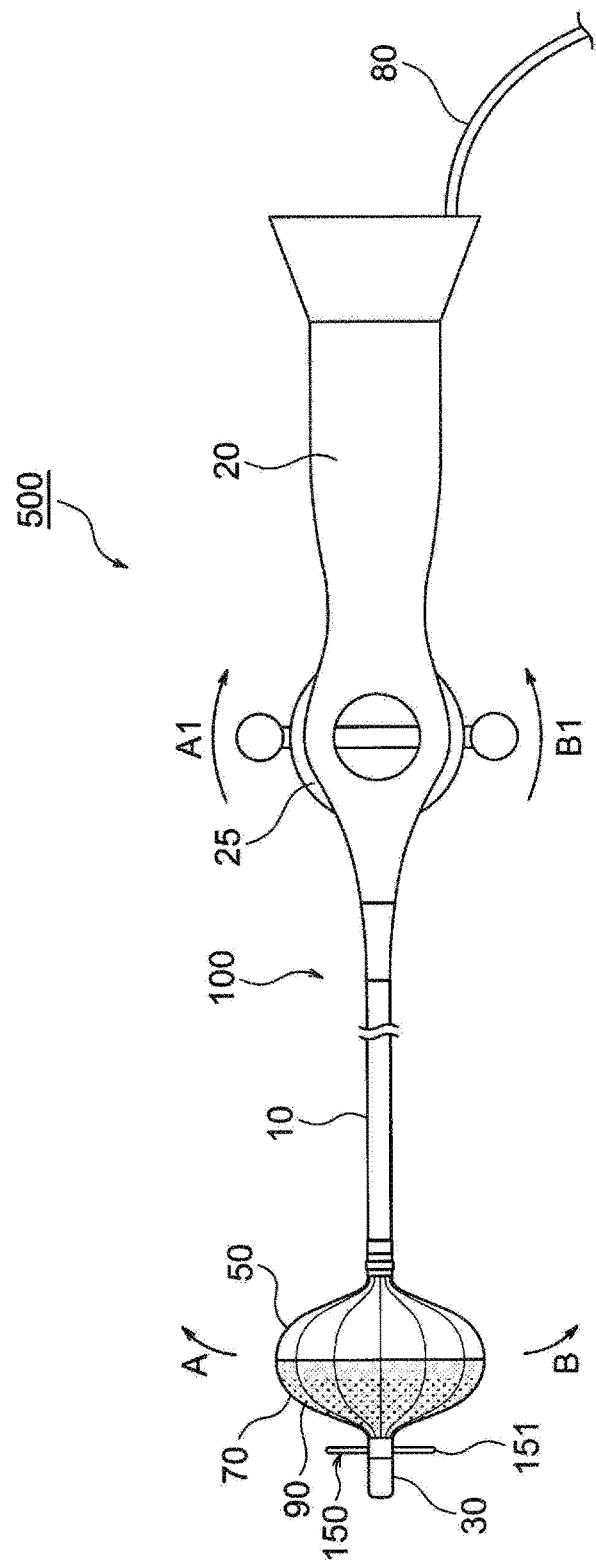
FIG. 10 is a schematic front view showing an embodiment of an ablation catheter device of the present invention.

Although not shown in FIG. 10, the proximal end side of the electrode catheter 150 (catheter main body 152) is inserted into the handle 20 through the second lumen 12 of the catheter shaft 10, and extends from this control handle 20. An operation handle is connected to the proximal end of the catheter main body 152.

Figure 11:
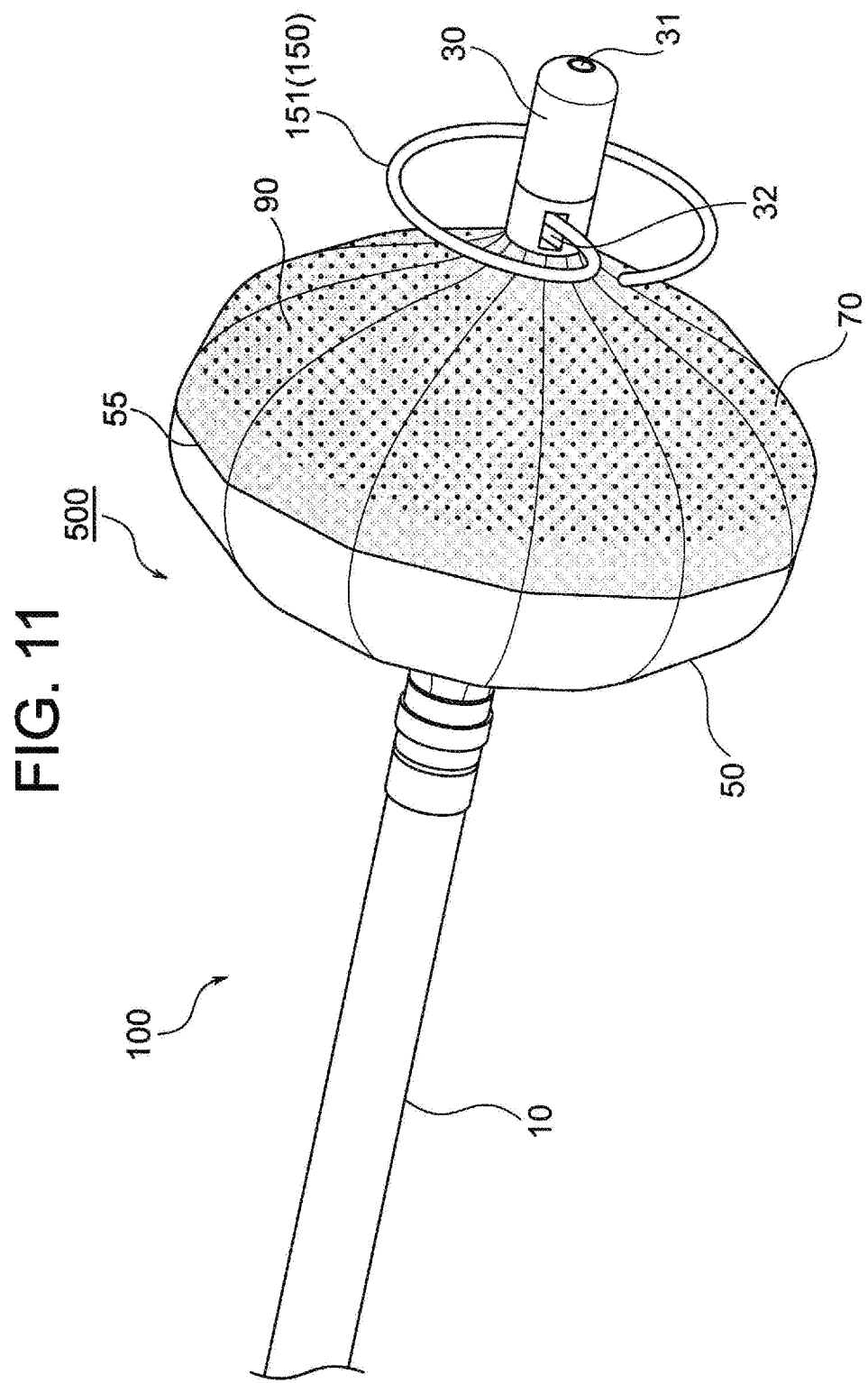
FIG. 11 is a perspective view showing the distal end part of the ablation catheter device shown in FIG. 10.
Figure 12:
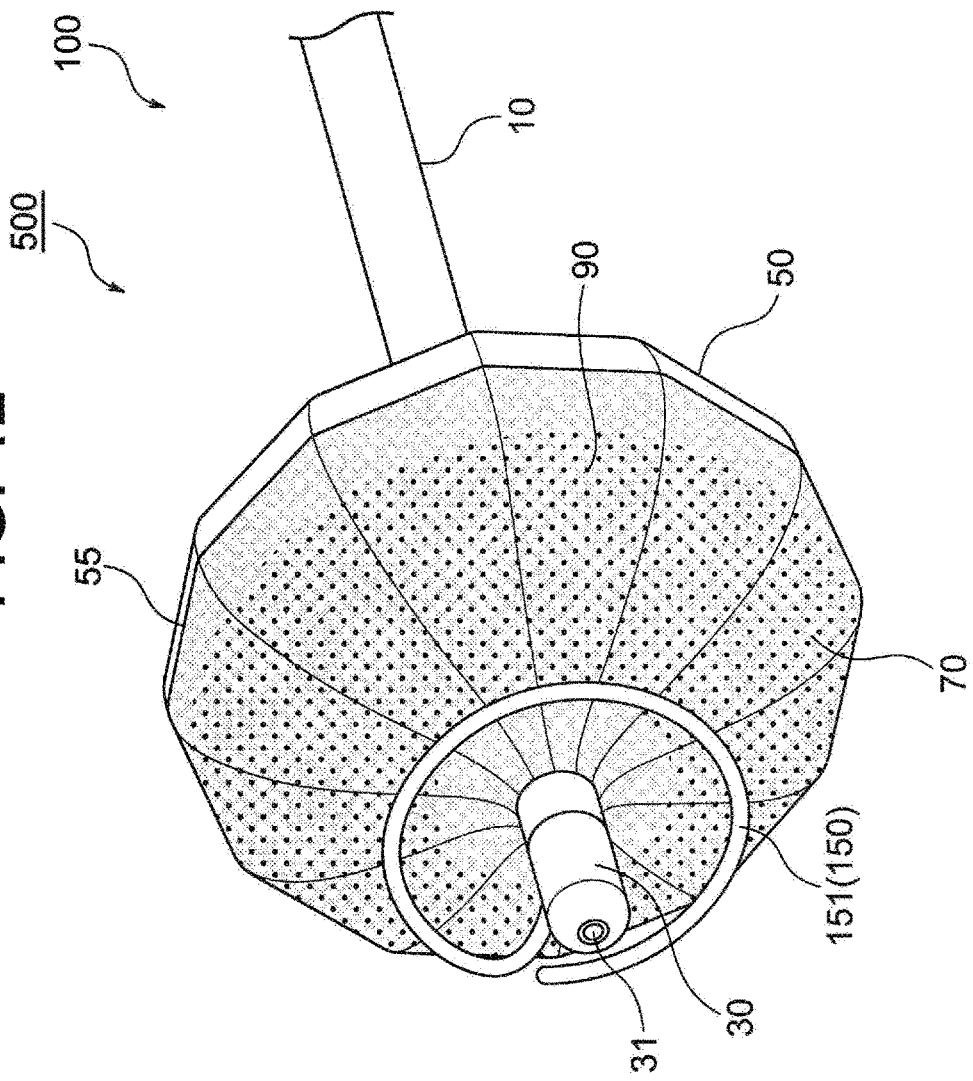
FIG. 12 is a perspective view showing the distal end part of the ablation catheter device shown in FIG. 10.
Figure 13:
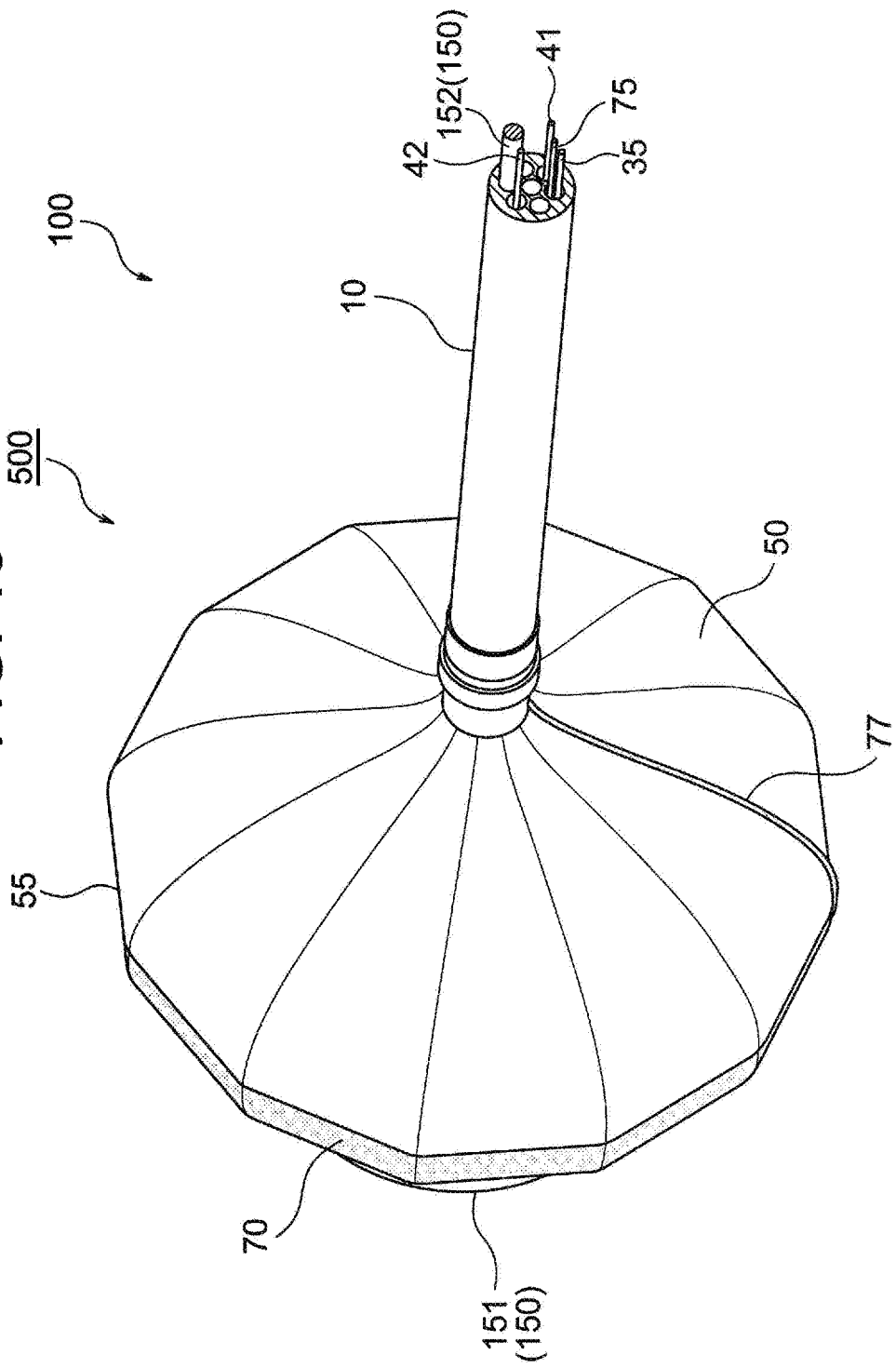
FIG. 13 is a perspective view showing the distal end part of the ablation catheter device shown in FIG. 10.

As shown in FIGS. 11 and 12, the catheter distal end part 151 of the electrode catheter 150 is formed in a ring-like shape, and a plurality of electrodes (not shown in the figure) are attached to the outer circumference of the catheter distal end part 151. The catheter distal end part 151 is easily deformed (for example, linearly deformed) by applying a force thereto, and returns to the ring-like shape when that force is removed.

The electrode catheter 150 for measuring the electric potential around the entire circumference of the pulmonary vein may be, for example, one described in Japanese Unexamined Patent Application Publication No. 2003-111740, and is preferably the electrode catheter described in Japanese Patent No. 4027411 filed by the applicant.

In the ablation catheter device 500 of this embodiment, the catheter distal end part 151 of the electrode catheter 150 passes through the side hole 32 formed in the distal end tip 30 of the ablation catheter 100, extends from the opening of the side hole 32 on the side peripheral surface of the distal end tip 30, and forms a ring-like shape. The catheter distal end part 151 can be retracted into the side hole 32 through the opening.

In the ablation treatment (procedure) performed using the ablation catheter device 500 of this embodiment, it is determined whether or not sufficient ablation is performed by measuring, with the electrode catheter 150, the electric potential around the entire circumference of the pulmonary vein before and after the ablation (current application) with the ablation catheter 100. If it is determined that abnormal electric potential before ablation disappears and sufficient ablation is performed, ablation treatment in the pulmonary vein is finished. If it is determined that abnormal electric potential does not disappear and ablation is insufficient, the balloon 50 is folded, and point-like ablation treatment (touch up) with the distal end tip 30 can be performed.

According to the ablation catheter device 500 of this embodiment, the electric potential around the entire circumference of the pulmonary vein at a position near the left atrium (a position near the ablation site) can be measured with the plurality of electrodes attached to the catheter distal end part 151 of the electrode catheter 150 in a state where the expanded balloon 50 that makes up the ablation catheter 100 is pressed against the area around the ostium of the pulmonary vein so as to cover the ostium of the pulmonary vein, and the effect of ablation treatment can be reliably ascertained from the change in the electric potential around the entire circumference of the pulmonary vein before and after ablation (current application).

According to this ablation catheter device 500, even during ablation treatment (during high-frequency current application), the electric potential around the entire circumference of the pulmonary vein on the left atrium side can be measured with the plurality of electrodes attached to the catheter distal end part 151 extending from the side hole 32 of the distal end tip 30, and therefore high-frequency current application can be stopped when disappearance of abnormal electric potential is seen, and excessive ablation can be prevented from being performed.

Although embodiments of the present invention has been described, the present invention is not limited to these, and various changes may be made.

For example, the high-frequency current application electrode need not be formed on the surface of the balloon, and may be provided inside the balloon or in the wall of the balloon. The present invention is also applicable to a balloon-type ablation catheter that performs ablation by heating liquid supplied to the inside of a balloon.

The balloon may have a shape other than a spheroidal shape (oblate spheroidal shape), and the part on the distal end side of the maximum diameter part and the part on the proximal end side of the maximum diameter part may differ in shape.

The distal end tip may not be an electrode.

REFERENCE SIGNS LIST 100 ablation catheter
10 catheter shaft
11 to 17 lumen
13A opening
16A opening
20 control handle
25 knob
30 distal end tip
31 guide wire lumen
32 side hole
35 conductor
41 first operation wire
42 second operation wire
50 balloon
55 maximum diameter part
70 high-frequency current application electrode
75 conductor 77 lead
80 injection tube
90 irrigation through-holes
150 electrode catheter
151 catheter distal end part
500 ablation catheter device

The invention claimed is:

1. A balloon-type ablation catheter comprising:
a catheter shaft in which a plurality of lumens are formed that include a liquid feeding lumen for flowing liquid and an electrode catheter insertion lumen for inserting an electrode catheter for measuring electric potential;
a distal end tip attached to a distal end of the catheter shaft;
a balloon that is attached to the catheter shaft so as to contain the distal end of the catheter shaft and that is expanded by supplying an inside surface thereof with liquid flowing through the liquid feeding lumen; and
a high-frequency current application electrode that is provided inside the balloon, on an outer surface of the balloon, or in a wall of the balloon, wherein high-frequency current is applied between the high-frequency current application electrode and a counter electrode plate configured to be attached to the body surface of a patient,
wherein a side hole that communicates with the electrode catheter insertion lumen and is formed to open in the distal end tip, the side hole extending radially from the distal end tip, positioned distally from the high-frequency current application electrode, on a side peripheral surface of a cylindrical linear body section of the distal end tip, and
wherein the entire side hole is positioned on the side peripheral surface of the cylindrical linear body section, and wherein a distal portion of the electrode catheter extends from the side hole in a direction perpendicular to the longitudinal axis of the catheter shaft and the distal portion is proximal to a distalmost surface of the distal end tip.

2. The balloon-type ablation catheter according to claim 1, wherein a distance (d) from the distal end of the balloon to the opening of the side hole is 4 mm or less.

3. The balloon-type ablation catheter according to claim 1,
wherein the high-frequency current application electrode is composed of a metal thin film formed on at least part of the outer surface of the balloon, and
wherein many irrigation through-holes leading from the inside surface of the balloon to a surface of the high-frequency current application electrode are formed in at least part of a region of the high-frequency current application electrode in order to irrigate the high-frequency current application electrode with liquid for expanding the balloon.

4. The balloon-type ablation catheter according to claim 1, wherein the distal end tip is an electrode.

5. An ablation catheter device comprising:
a balloon-type ablation catheter comprising:
a catheter shaft in which a plurality of lumens are formed that include a liquid feeding lumen for flowing liquid and an electrode catheter insertion lumen for inserting an electrode catheter for measuring electric potential;
a distal end tip attached to a distal end of the catheter shaft;
a balloon that is attached to the catheter shaft so as to contain the distal end of the catheter shaft and that is expanded by supplying an inside surface thereof with liquid flowing through the liquid feeding lumen; and
a high-frequency current application electrode that is provided inside the balloon, on an outer surface of the balloon, or in a wall of the balloon, wherein high-frequency current is applied between the high-frequency current application electrode and a counter electrode plate configured to be attached to the body surface of a patient,
wherein a side hole that communicates with the electrode catheter insertion lumen and is formed to open in the distal end tip, the side hole extending radially from the distal end tip, positioned distally from the high-frequency current application electrode, on a side peripheral surface of a cylindrical linear body section of the distal end tip, and wherein the entire side hole is positioned on the side peripheral surface of the cylindrical linear body section, and wherein a distal portion of the electrode catheter extends from the side hole in a direction perpendicular to the longitudinal axis of the catheter shaft and the distal portion is proximal to a distalmost surface of the distal end tip, and
the electrode catheter for measuring the electric potential around an entire circumference of a pulmonary vein inserted into the electrode catheter insertion lumen of the catheter shaft that makes up the balloon-type ablation catheter,
wherein the electrode catheter includes a catheter main body, and a ring-like catheter distal end part connected to the catheter main body and having a plurality of electrodes, and
wherein the ring-like catheter distal end part of the electrode catheter is inserted into the side hole formed in the distal end tip of the balloon-type ablation catheter, and can be caused to extend from the side hole and can be retracted.

* * * * *